(12) United States Patent
Ueda et al.

(10) Patent No.: US 9,089,680 B2
(45) Date of Patent: Jul. 28, 2015

(54) CONNECTOR

(71) Applicant: Terumo Kabushiki Kaisha, Tokyo (JP)

(72) Inventors: Yasuhiro Ueda, Yamanashi (JP);
Yasunobu Zushi, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/226,425

(22) Filed: Mar. 26, 2014

(65) Prior Publication Data

US 2014/0207117 A1    Jul. 24, 2014

Related U.S. Application Data

(63) Continuation of application No. PCT/JP2012/071041, filed on Aug. 21, 2012.

(30) Foreign Application Priority Data

Sep. 27, 2011    (JP) ................................. 2011-210214

(51) Int. Cl.
| | | |
|---|---|---|
| *A61M 25/16* | (2006.01) | |
| *A61M 25/18* | (2006.01) | |
| *A61M 39/00* | (2006.01) | |
| *A61M 39/10* | (2006.01) | |
| *A61M 39/02* | (2006.01) | |

(52) U.S. Cl.
CPC .............. *A61M 39/10* (2013.01); *A61M 39/02* (2013.01)

(58) Field of Classification Search
CPC .......... A61M 39/223; A61M 2206/20; A61M 2039/0205; A61M 39/02; A61M 39/10; A61M 1/0035; A61M 1/0058; A61M 5/4405; A61M 25/0014; A61M 39/04; A61M 5/14228; A61M 5/145; A61M 5/16827

USPC ........................................................ 604/533
See application file for complete search history.

(56) References Cited

U.S. PATENT DOCUMENTS

| | | | |
|---|---|---|---|
| 2007/0233046 A1 | 10/2007 | Funamura et al. | |
| 2007/0255202 A1* | 11/2007 | Kitani et al. | .................... 604/82 |
| 2008/0086097 A1 | 4/2008 | Rasmussen et al. | |

FOREIGN PATENT DOCUMENTS

| | | |
|---|---|---|
| JP | 2006-129884 A | 5/2006 |
| JP | 2007-175477 A | 7/2007 |
| JP | 2007-313279 A | 12/2007 |
| JP | 2010-505551 A | 2/2010 |

OTHER PUBLICATIONS

International Search Report dated Oct. 23, 2012 issued in International Application No. PCT/JP2012/071041.

* cited by examiner

*Primary Examiner* — Jason Flick
(74) *Attorney, Agent, or Firm* — Foley & Lardner LLP

(57) ABSTRACT

A connector comprises a housing; a main flow path being configured such that fluid is flowable from a first tube through the main flow path into a second tube; and a connection terminal including a connection side space, the connection terminal being configured such that a third tube is connectable to the connection terminal and an auxiliary flow path of the third tube communicates with the main flow path via the connection side space. The main flow path includes a main flow path side space that is continuous with at least the connection side space and is defined by: a bottom part facing the connection side space and a pair of side parts extending from opposite sides of the bottom part toward the connection side space, and at least one wall surface configured to direct the fluid toward the connection side space and toward at least one of the side parts.

7 Claims, 9 Drawing Sheets

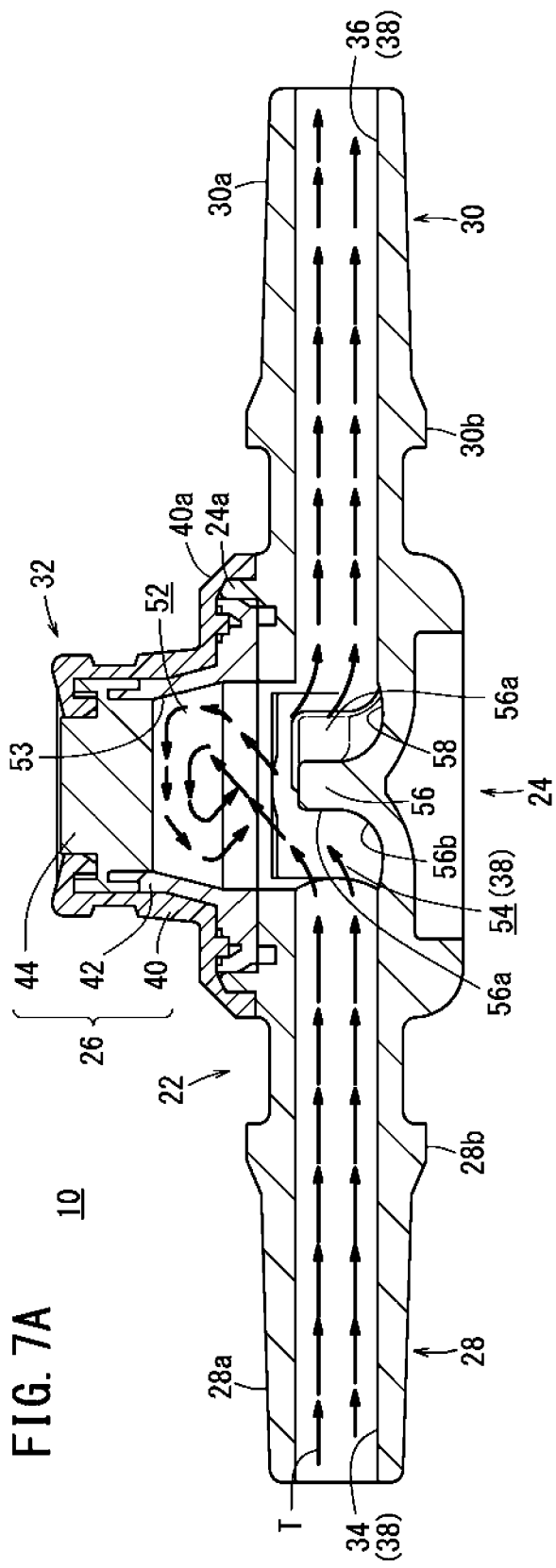
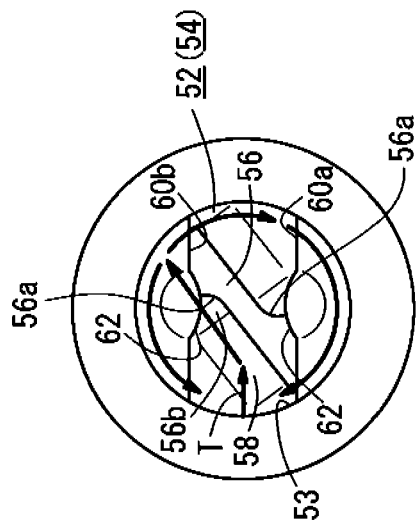

CONNECTOR

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/071041 filed on Aug. 21, 2012, which is based upon and claims the benefit of priority of Japanese Application No. 2011-210214 filed on Sep. 27, 2011, the entire contents of which are hereby incorporated by reference in their entireties.

BACKGROUND

1. Technical Field

The present disclosure relates to a connector that connects a plurality of tubes to each other, for example, in an infusion line for performing fluid infusion to a patient.

2. Background Art

Conventionally, when performing fluid infusion to a patient, a plurality of tubes are connected to construct an infusion line which is continuous from an infusion bag as a supply source of an infusion fluid up to the patient, and a connector is used as a tool for connecting the tubes to each other. In fluid infusion, with respect to a main line for supplying a main infusion fluid to a patient, another infusion fluid may be supplied from an auxiliary line, and these infusion fluids may be mixed in a connector and directed to the patient. In this case, a connector including a three-way port which can allow an infusion fluid to flow therethrough is used (refer, for example, to Japanese Unexamined Patent Application Publication No. JP 2010-505551).

The connector includes a housing which has a main line flow path formed therein. A connection terminal to which a plug (tube terminal) of an auxiliary line is connected is formed in a body part of the housing. In this case, a plug housing space (hereinbelow, referred to as a connection side space) which is continuous with the main line flow path is provided inside the connection terminal due to the necessity of connecting a standardized plug thereto.

The connection side space is formed at a position deviated from the main line flow path in order to ensure the insertability of the plug. Therefore, a phenomenon occurs in which fluid (liquid, gas, or the like) existing in the connection side space stagnates in the connection side space. Such fluid stagnating in the connection side space (hereinbelow, also referred to as stagnating fluid in order to distinguish it from fluid flowing in the main line flow path) may disadvantageously cause various troubles, in particular, in medical instruments.

For example, before supplying an infusion fluid to a patient, an operation of filling up the infusion fluid inside an infusion line to remove air therefrom (also referred to as priming) is performed. However, air bubbles (air) may stagnate in a connection side space of a connector. As a result, when supplying the infusion fluid to the patient, the air bubbles remaining therein may be disadvantageously introduced into the patient together with the infusion fluid. In addition, when supplying a high nutritive liquid as an infusion fluid, the liquid stagnates inside the connection side space, and bacteria may thereby grow inside the connector. As a result, the bacteria may be disadvantageously introduced into a patient. Further, when changing an infusion fluid supplied to a patient to a next infusion fluid, if the next infusion fluid is supplied with the previously supplied infusion fluid stagnating in the connection side space, these different infusion fluids may be disadvantageously mixed and introduced into a patient.

In order to prevent the troubles as described above, in the connector disclosed in JP 2010-505551, a wall (fluid flow director) is provided on the main line flow path. Specifically, an infusion fluid flowing through the main line flow path is guided to the connection side space by the wall, and discharge of stagnating fluid is accelerated by the infusion fluid.

However, even when the wall is provided in a midway part of the main line flow path, and an infusion fluid is thereby guided to the connection side space as in the connector of JP 2010-505551, the infusion fluid is mixed into stagnating fluid that is previously filled inside the connection side space, and it is therefore difficult to discharge the stagnating fluid. That is, even if an infusion fluid is simply guided, the guided infusion fluid can affect only a part of stagnating fluid. Therefore, the stagnating fluid still remains left in the connection side space, and the above troubles may occur.

Thus, there is a need for a connector that can efficiently discharge fluid stagnating in a connection side space in a connection terminal from the connection side space with a simple configuration, thereby enhancing the safety of fluid infusion and correctly supplying a desired fluid.

SUMMARY OF INVENTION

In one embodiment, a connector comprises a housing; a flow path which is provided inside the housing and allows fluid flowing from a first tube to flow therethrough into a second tube; and a connection terminal which has a connection side space continuous with the flow path and is capable of connecting thereto a third tube through the connection side space. In the connector, the flow path includes a flow path side space which is continuous with at least the connection side space and defined by a bottom part facing the connection side space and a pair of side parts extending from opposite sides of the bottom part toward the connection side space, and at least one wall surface directing the fluid to the connection side space so as to flow toward at least one of the side parts.

With the above configuration, since the wall surface which directs fluid to the connection side space so as to flow toward at least one of the side parts, the fluid can be guided so that turbulence of stagnating fluid existing inside the connection side space is made large to accelerate the flow. Therefore, fluid stagnating inside the connection side space can be easily discharged from the connection side space by the fluid guided by the wall surface. As a result, when constructing an infusion line which administers an infusion fluid using the connector, the safety of fluid infusion can be significantly enhanced, and a desired infusion fluid can be excellently supplied to a patient.

In this case, it is preferred that the at least one wall surface be provided on the bottom part so as to extend obliquely with respect to an axial direction of the flow path in plan view, and opposite ends of the at least one wall surface be coupled to the respective side parts.

In this manner, since the wall surface is provided on the bottom part so as to extend obliquely with respect to the axial direction of the flow path in plan view, and the opposite ends of the wall surface is coupled to the respective side parts, the entire fluid flowing in the axial direction of the flow path can be directed to one of the side parts. Further, the fluid directed to one direction is guided to the connection side space, thereby making it possible to make the turbulence of fluid inside the connection side space larger to accelerate the flow.

As a result, it is possible to more efficiently discharge the stagnating fluid inside the connection side space.

The at least one wall surface may include a top part between the side parts in plan view and may be provided on the bottom part so as to extend from the top part obliquely with respect to an axial direction of the flow path, and opposite ends of the at least one wall surface may be coupled to the respective side parts.

In this manner, since the wall surface includes the top part between the side parts in plan view and is provided on the bottom part so as to extend from the top part obliquely with respect to the axial direction of the flow path, and the opposite ends of the wall surface are coupled to the respective side parts, fluid flowing in the axial direction of the flow path can be divided into two directions from the top part and directed to the pair of side parts. Further, even when the fluid directed to the two directions is guided to the connection side space, it is possible to make the turbulence of fluid inside the connection side space large to accelerate the flow.

The at least one wall surface may be formed into a curved shape at a coupled part with the bottom part.

In this manner, since the coupled part of the wall surface is formed into a curved shape, even fluid flowing on the side of the bottom part of the flow path can be easily guided to the connection side space. Therefore, the amount of fluid guided to the connection side space increases, thereby making it possible to make the turbulence of fluid inside the connection side space further larger.

The at least one wall surface may include a plurality of wall surfaces which are provided in a rib dividing the flow path in plan view on both sides facing the divided two flow paths.

In this manner, since the wall surfaces are formed on both sides of the rib, the both sides facing the two flow paths divided by the rib, in either case where each of the two fluid flow ports formed in the housing is attached to the first tube or the second tube, fluid can be guided so as to generate a large flow inside the connection side space by either one of the wall surfaces. As a result, connection of the connector can be simplified.

Each of the side parts preferably has a constricted portion which inwardly extends so as to gradually narrow the width of the flow path side space.

In this manner, since the width of the flow path side space is gradually narrowed by the constricted portion, it is possible to temporarily guide fluid flowing in the flow path side space to the inner side to thereby increase the amount of fluid directed to one of the side parts by the wall surface. As a result, it is possible to generate a larger flow inside the connection side space.

According to embodiments of the present invention, it is possible to efficiently discharge fluid stagnating in a connection side space in a connection terminal from the connection side space with a simple configuration, thereby enhancing the safety of fluid infusion and excellently supplying a desired fluid.

BRIEF DESCRIPTION OF DRAWINGS

FIG. 7A is a side cross-sectional view schematically illustrating the flow of an infusion fluid in the connector according to the first embodiment; and FIG. 7B is a main part enlarged plan view schematically illustrating the flow of an infusion fluid in the connector according to the first embodiment.

DESCRIPTION OF EMBODIMENTS

Hereinbelow, a connector according to embodiments of the present invention will be described in detail on the basis of a relationship with a fluid infusion set to which the connector can be applied. Needless to say, the application of the connector is not limited to application to the fluid infusion set.

Figure 1:
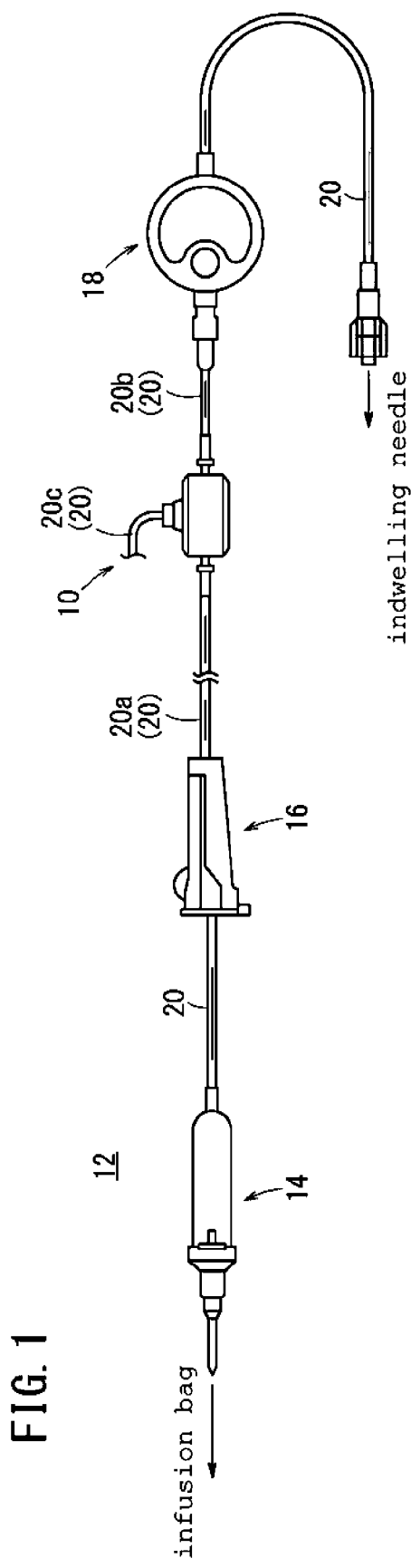
FIG. 1 is an explanatory diagram schematically illustrating an example of a fluid infusion set to which a connector according to the present invention is applied.

FIG. 1 is an explanatory diagram schematically illustrating an example of a fluid infusion set 12 to which a connector 10 according to the present invention is applied.

As already described, the connector 10 has a function of connecting a plurality of tubes to each other in an infusion line for performing fluid infusion to a patient. For example, the connector 10 is applied to the fluid infusion set 12 as illustrated in FIG. 1. The fluid infusion set 12 has an upstream end which is connected to an infusion bag (not illustrated) and a downstream end which is connected to an indwelling needle (not illustrated). Accordingly, an infusion line that can administer (supply) an infusion fluid T (fluid: refer to FIG. 7) to a patient is constructed.

Examples of the infusion fluid T include any fluids that can be administered to a living body such as a drug solution, a corrective electrolyte solution, and saline. When the infusion fluid is a drug solution, for example, various kinds of drugs such as a sedative, an intravenous anesthetic, an anesthetic sedative, a local anesthetic, a nondepolarizing muscle relaxant, a pressor agent, an antihypertensive agent, a coronary vasodilator, a diuretic agent, an antiarrhythmic agent, a bronchodilator, a hemostatic agent, a vitamin compound, an antibiotic, and a fat emulsion can be applied.

As illustrated in FIG. 1, the fluid infusion set 12 includes a drip tube 14 which allows the amount of flow of the infusion fluid T (refer to FIG. 7) supplied from the infusion bag to be visually confirmed, a clamp (also referred to as a klemme) 16 which adjusts the amount of flow of the infusion fluid T, an air vent filter 18 which discharges (or supplies) air existing in the infusion line, and the like. A tube 20 which can allow the infusion fluid T to flow therethrough is connected (or inserted through) between the components. The fluid infusion set 12 is, of course, not limited to the configuration illustrated in FIG. 1. Various components (an infusion pump and a check valve, for example) which are arranged in the infusion line other than the above components can be attached to the fluid infusion set 12.

The tube 20 of the fluid infusion set 12 is a tube body having flexibility, and constitutes the infusion line through which the infusion fluid T actually flows. Examples of the constituent material of the tube 20 include soft polyvinyl chloride, ethylene-vinyl acetate copolymers, polyethylene, polypropylene, polybutadiene, and materials mainly composed of these materials.

When the connector 10 is applied to the fluid infusion set 12 as described above, the connector 10 is arranged, for example, between the clamp 16 and the air vent filter 18. That is, the connector 10 has a function to connect a first tube 20a which is connected to the downstream side of the clamp 16 and a second tube 20b which is connected to the upstream side of the air vent filter 18 to each other to thereby allow the infusion fluid T to flow from the first tube 20a to the second tube 20b. Further, the connector 10 is a three-port connector to which a third tube 20c which is formed, with respect to a main line formed by the first tube 20a and the second tube 20b, as an auxiliary line can be connected.

The fluid infusion set 12 does not particularly limit an arrangement position of the connector 10. When constructing the infusion line, the connector 10 can be arranged at a desired position. Further, it is needless to say that the number of connectors 10 is not limited to one, and a plurality of connectors 10 can be arranged in the fluid infusion set 12 (infusion line). For example, two connectors 10 can be arranged between the clamp 16 and the air vent filter 18 and the downstream side of the air vent filter 18.

Hereinbelow, the connector 10 and a connector 10A according to the present invention which are applied to the above infusion line will be specifically described by giving preferred embodiments (first and second embodiments).

First Embodiment

Figure 2:
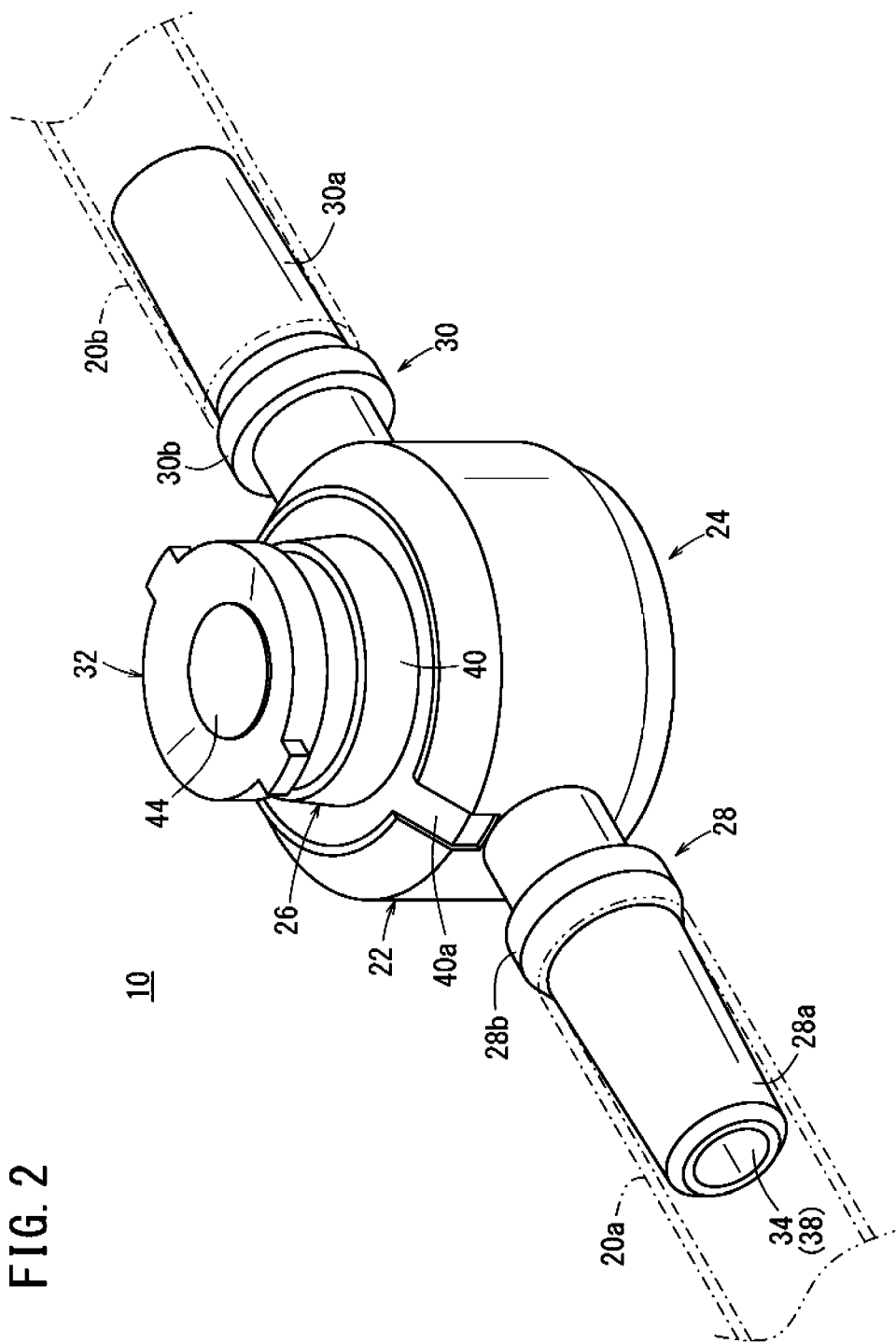
FIG. 2 is a perspective view illustrating the entire configuration of a connector according to a first embodiment.
Figure 3:
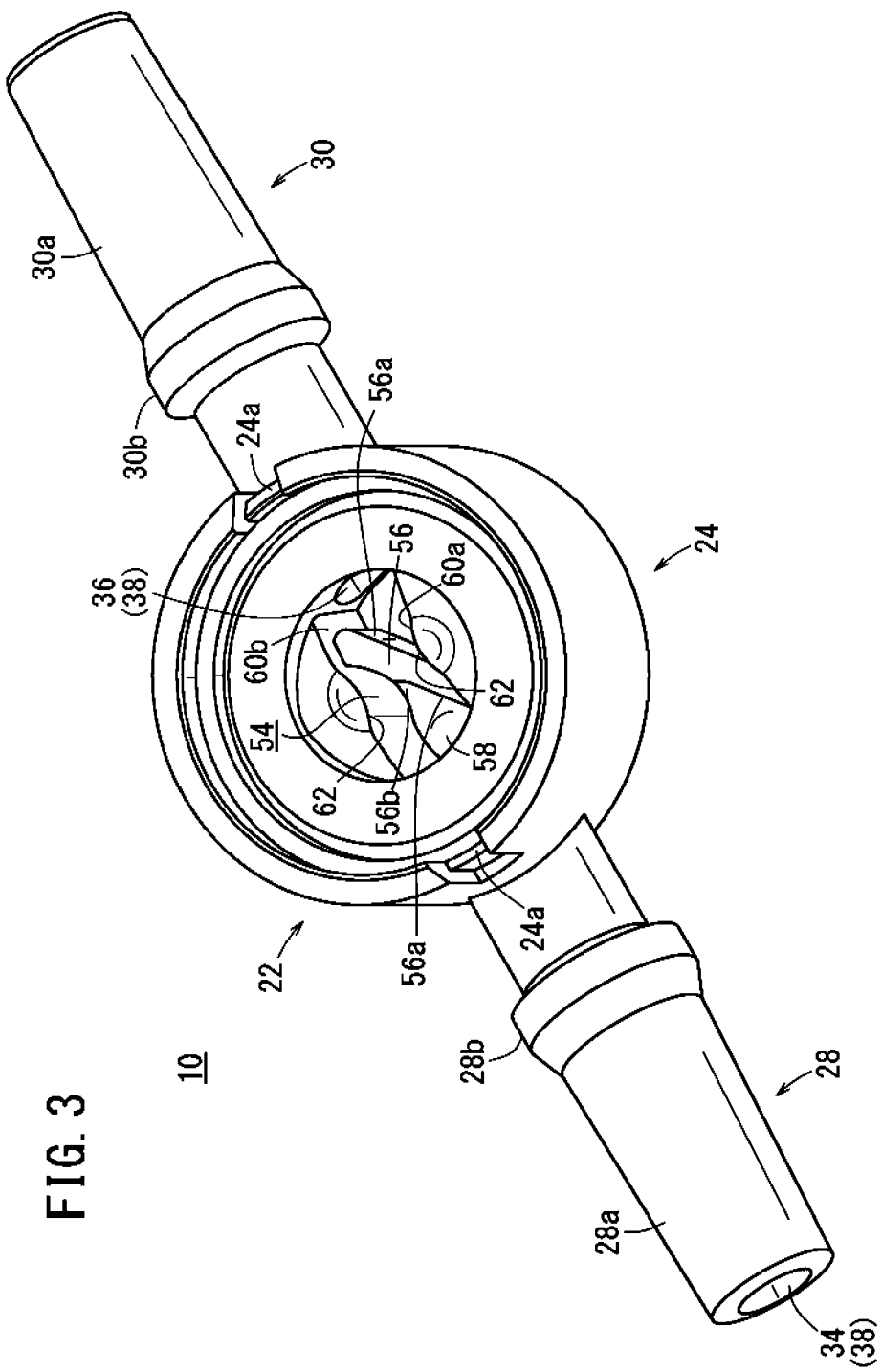
FIG. 3 is a perspective view illustrating the connector of FIG. 2 with a lid detached therefrom.
Figure 4:
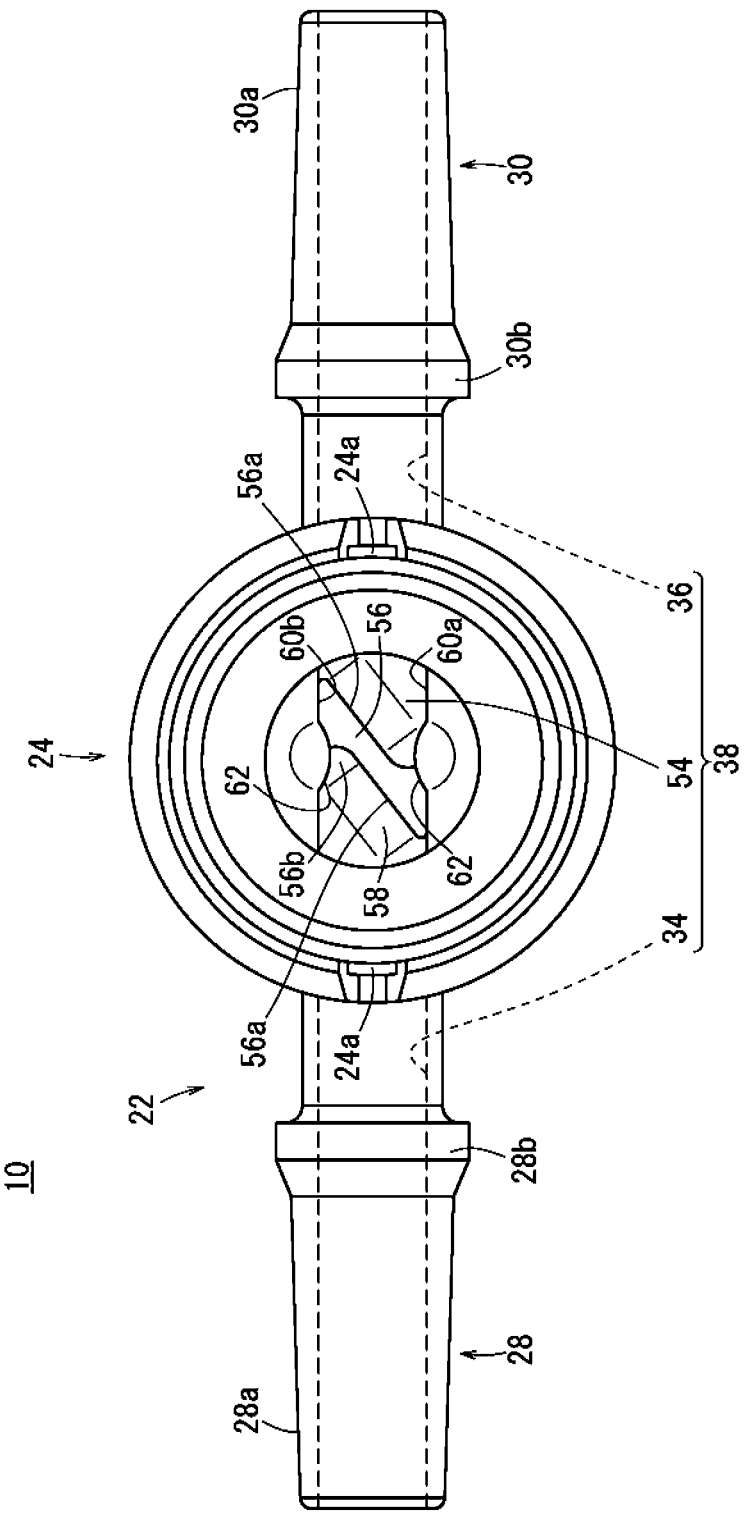
FIG. 4 is a plan view of the connector of FIG. 3.
Figure 5:
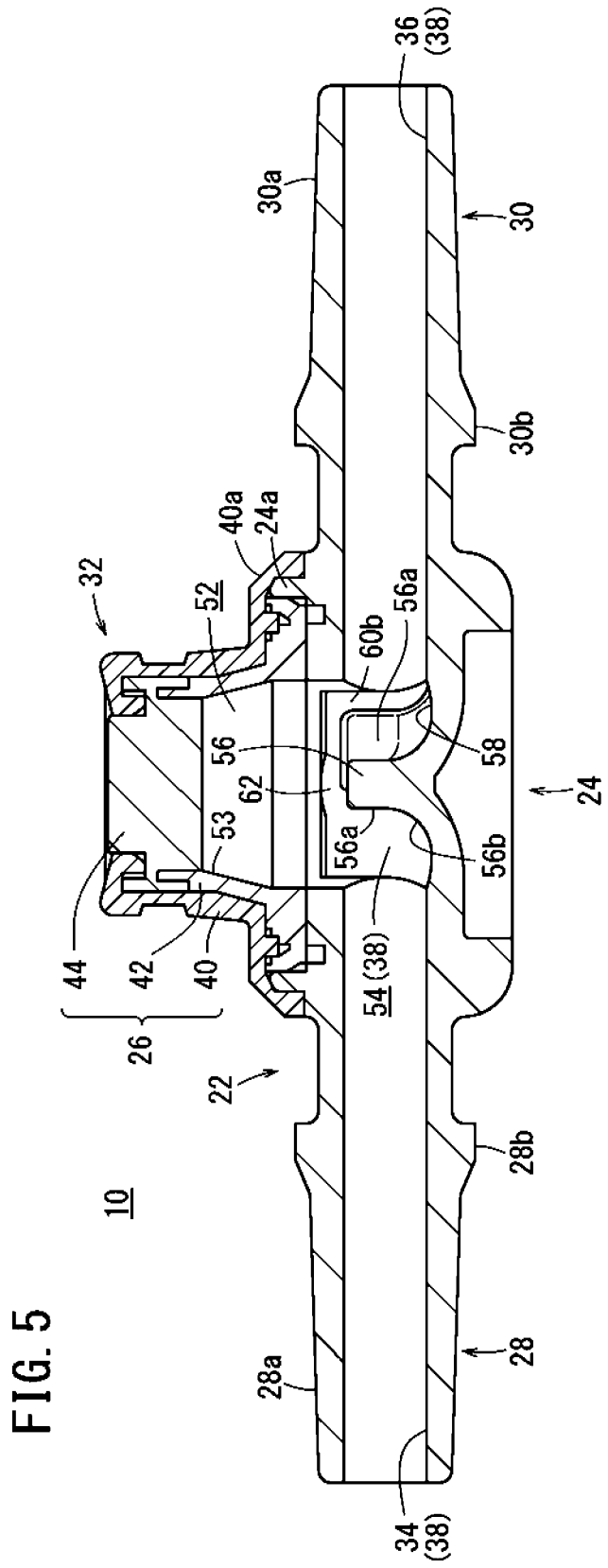
FIG. 5 is a side cross-sectional view of the connector of FIG. 2.

FIG. 2 is a perspective view illustrating the entire configuration of the connector 10 according to the first embodiment. FIG. 3 is a perspective view illustrating the connector 10 of FIG. 2 with a lid 26 detached therefrom. FIG. 4 is a plan view of the connector 10 of FIG. 3. FIG. 5 is a side cross-sectional view of the connector 10 of FIG. 2.

As illustrated in FIG. 2, the connector 10 includes a housing 22 which has a flow path of an infusion line (including a main line and auxiliary line) formed inside thereof. The housing 22 is formed of a resin material that is hard relative to the tube 20 having flexibility. Examples of the constituent material of the housing 22 include polyethylene, polypropylene, polyolefin such as ethylene-vinyl acetate copolymers, polyurethane, polyamide, polyester, polycarbonate, polybutadiene, and polyvinyl chloride.

The housing 22 includes a connector base 24 having a bottomed tubular shape, the lid 26 which is attached to the connector base 24 so as to block an upper side opening of the connector base 24, and a first port 28 and a second port 30 each of which is coupled to the side peripheral surface of the connector base 24. In this case, the first tube 20a is connected to the first port 28, and the second tube 20b is connected to the second port 30. A third port (connection terminal) 32 to which the third tube 20c is connected is arranged continuous with the upper surface of the lid 26.

As illustrated in FIGS. 2 to 5, the first port 28 is formed into a generally cylindrical shape. The first port 28 has a proximal end which is continuous with the connector base 24 and a tip end which linearly extends toward the upstream side of the infusion line. An inner cavity of the first port 28 serves as a first port flow path 34 which can allow the infusion fluid T to flow therethrough (refer to FIG. 5).

The outer shape of the first port 28 is formed into a male luer taper. The first port 28 is inserted into the first tube 20a (the inner cavity of the first tube 20a). That is, a tapered surface 28a whose diameter slightly expands from the tip end toward the proximal end is formed on the outer peripheral surface of the first port 28. Accordingly, the tip end of the first port 28 can be easily inserted into the first tube 20a when the first port 28 is connected to the first tube 20a. Further, a projection 28b is formed on the proximal side with respect to the tapered surface 28a. Accordingly, by allowing the first tube 20a to advance beyond the projection 28b, the first tube 20a does not easily come off, and the first tube 20a and the first port 28 can be liquid-tightly connected to each other.

On the other hand, the second port 30 is coupled to the connector base 24 on the opposite side of the first port 28. The second port 30 has a proximal end which is continuous with the connector base 24 and a tip end which linearly extends toward the downstream side of the infusion line. That is, the first port 28 and the second port 30 are formed so as to be linearly arranged in a row with their axes coincide with each other in plan view (refer to FIG. 4). An inner cavity of the second port 30 serves as a second port flow path 36 which can allow an infusion fluid to flow therethrough (refer to FIG. 5).

The second port 30 is formed into the same shape as the first port 28 (a male luer taper having a tapered surface 30a and a projection 30b on the outer peripheral surface thereof), and can obtain the same effect as the first tube 20a when being connected to the second tube 20b. A method of connecting the first and second tubes 20a and 20b and the first and second ports 28 and 30 is not limited to the present embodiment. For example, connection mechanisms may be provided on the distal ends of the first and second tubes 20a and 20b and the distal ends of the first and second ports 28 and 30 to achieve easy attachment/detachment.

In the connector 10, the first port flow path 34 and the second port flow path 36 serve as a flow path of a main line of the infusion fluid T (hereinbelow, referred to as a main line flow path 38). That is, the main line flow path 38 is formed so that an extension line of the axis of the first port flow path 34 (in the axial direction) and an extension line of the axis of the second port flow path 36 (in the axial direction) coincide with each other in plan view and side view.

As illustrated in FIG. 5, the third port 32 is formed in a direction perpendicular to the axial direction of the first port 28 and the second port 30. In other words, the connector 10 according to the first embodiment is configured as a T-shaped connector in which the branch angle of the third port 32 with respect to the main line flow path 38 is 90 degree. The third port 32 allows an infusion fluid supplied through the third tube 20c to join the infusion fluid T flowing in the main line flow path 38.

The lid 26 in which the third port 32 is formed is configured as a single unit which includes an outer casing 40, an inner casing 42, and a valve 44. Each of the outer casing 40 and the inner casing 42 is formed as a cylindrical body. An end of each of the outer casing 40 and the inner casing 42, the end being connected to the connector base 24, forms a flange portion extending in the outer diameter direction. The lid 26 is attached to the upper side of the connector base 24 so that the outer casing 40 covers the outer peripheral surface and the upper surface of the inner casing 42. When attaching the lid 26 to the connector base 24, a pair of locking claws 40a which are provided in the outer casing 40 (flange portion) along the formation direction of the first port 28 and the second port 30 are hooked on engagement portions 24a of the connector base 24 to thereby hold the engagement portions 24a by the locking claws 40a and the outer edge of the inner casing 42. As a result, it is possible to firmly fix the lid 26 to the connector base 24.

The valve 44 is formed of an elastic material. The peripheral edge of the valve 44 is interposed between the outer casing 40 and the inner casing 42, so that the valve 44 is held on the upper part of the lid 26. The valve 44 self-blocks the third port 32 when the third tube 20c is not connected. On the other hand, when the third tube 20c is connected, the valve 44 is elastically deformed in response to the entrance of a plug 46 (refer to FIG. 6) to thereby liquid-tightly connect the plug 46 thereto.

The third port 32 is formed so as to have a predetermined thickness by stacking the cylindrical bodies of the outer casing 40 and the inner casing 42 in the diameter direction. In this case, an opening on one end of the third port 32 is connected to the main line flow path 38 of the connector base 24. The valve 44 is arranged on an opening on the other end of the third port 32.

Figure 6:
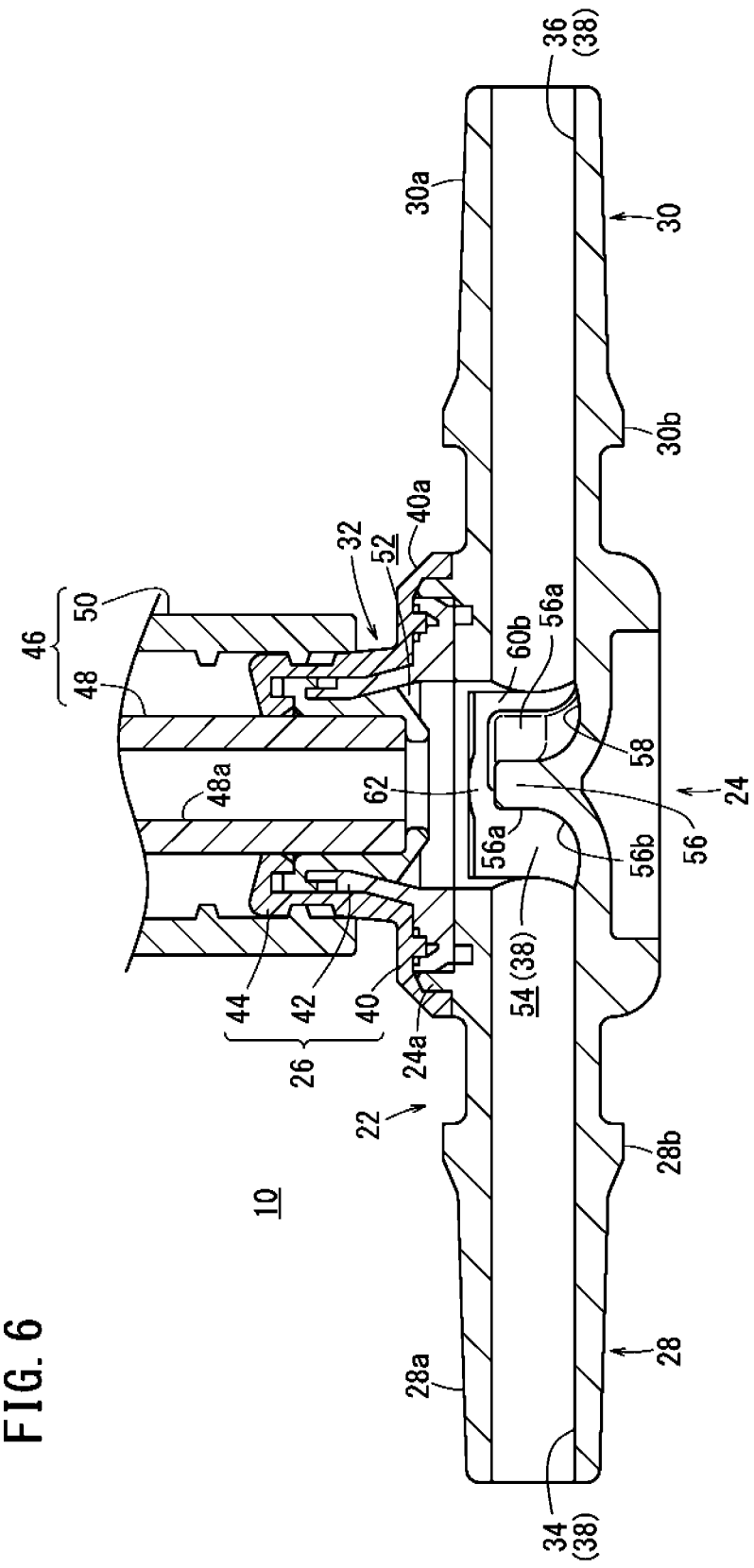
FIG. 6 is a side cross-sectional view illustrating a state where a plug of a third tube is connected to a third port of the connector of FIG. 5.

FIG. 6 is a side cross-sectional view illustrating a state where the plug 46 of the third tube 20c is connected to the third port 32 of the connector 10 of FIG. 5.

As illustrated in FIG. 6, the plug 46 of the third tube 20c is inserted into the third port 32. The plug 46 is standardized, for example, by ISO. Specifically, the plug 46 of the third tube 20c includes an inner tube 48 which has a flow path of an auxiliary line of the infusion fluid T (hereinbelow, referred to as auxiliary line flow path 48a) inside thereof and an outer tube 50 which surrounds the inner tube 48. The plug 46 holds the third port 32 between the outer periphery of the inner tube 48 and the inner periphery of the outer tube 50.

On the other hand, the third port 32 has a connection side space 52 which can attach and hold the plug 46. The connection side space 52 is surrounded by an inner wall 53 (refer to FIG. 5) of the inner casing 42 which forms the cylindrical body. The inner tube 48 of the plug 46 is inserted into the connection side space 52 so as to push the valve 44 thereinto. Accordingly, the valve 44 and the inner tube 48 are liquid-tightly fitted to and held by the inner wall 53 of the inner casing 42, and the auxiliary line flow path 48a communicates with the main line flow path 38 through the connection side space 52.

As illustrated in FIG. 5, when the valve 44 self-blocks the third port 32 (that is, when the plug 46 is not inserted into the third port 32), the connection side space 52 is formed as a space having a predetermined volume by the valve 44 and the inner wall 53. Further, the connection side space 52 is provided continuous with the linearly formed main line flow path 38 so as to be deviated upward from the main line flow path 38 in side view. Therefore, when the plug 46 is not inserted into the third port 32, the infusion fluid T flowing in the main line flow path 38 flows into the connection side space 52.

The lid 26 which has the third port 32 having the above configuration is attached to the upper side opening of the connector base 24 which is formed into a bottomed tubular shape (refer to FIG. 2). As illustrated in FIG. 3, a flow path groove (flow path side space) 54 is provided inside the connector base 24. The flow path groove 54 penetrates the connector base 24 along the axial direction of the first port 28 and the second port 30 (linearly). Further, as described above, the pair of engagement portions 24a on which the locking claws 40a are hooked are formed on the upper side of the side peripheral wall of the connector base 24 in the formation direction of the first port 28 and the second port 30.

In a state where the lid 26 is attached to the connector base 24, the flow path groove 54 is continuous with the connection side space 52. Accordingly, an integrated space is formed in a central part of the connector 10 by the connection side space 52 and the flow path groove 54 (refer to FIG. 5).

The flow path groove 54 includes a bottom part 58 which faces the connection side space 52 and a pair of side parts 60a and 60b which extend from opposite sides of the bottom part 58 toward the connection side space 52. The first port flow path 34 communicates with one end in the extending direction of the flow path groove 54, and the second port flow path 36 communicates with the other end thereof. That is, the main line flow path 38 of the connector 10 includes the first port flow path 34, the flow path groove 54, and the second port flow path 36 in this order from the upstream side toward the downstream side. These flow paths (and the groove) are linearly formed so as to be continuous with each other.

A rib 56 which extends obliquely with respect to the axial direction of the main line flow path 38 is formed on the bottom part 58 of the flow path groove 54 at an intermediate position in the extending direction of the flow path groove 54. The rib 56 is formed so as to be lower than the side parts 60a and 60b of the flow path groove 54, and has a function to direct the infusion fluid T flowing through the main line flow path 38 to the downstream side and, at the same time, guide the infusion fluid T to the connection side space 52 located above along a wall surface 56a. In the rib 56 according to the first embodiment, one end thereof is coupled to the side part 60a and the coupled part therebetween is located on the upstream side with respect to the center in the extending direction of the flow path groove 54, and the other end thereof is coupled to the side part 60b and the coupled part therebetween is located on the downstream side with respect to the center in the extending direction of the flow path groove 54.

The rib 56 includes wall surfaces 56a on both sides facing the first port flow path 34 and the second port flow path 36. Each of these wall surfaces 56a is formed on the bottom part 58 so as to extend obliquely with respect to the axial direction of the main line flow path 38 in plan view (refer to FIG. 4) on the basis of the shape of the rib 56. The respective ends of each of the wall surfaces 56a are coupled to the side parts 60a and 60b. Therefore, when viewed from the upstream side of the flow path groove 54, each of the wall surfaces 56a is formed so that one end thereof which is coupled to the side part 60a is located on the front side and the other end thereof which is coupled to the side part 60b is located on the depth side.

As illustrated in FIG. 5, a part of the rib 56, the part being coupled to the bottom part 58, is formed into a curved shape (a curved portion 56b). The curved portion 56b has a function to smoothly guide the infusion fluid T which flows from the upstream side to the rib 56 to the connection side space 52 located above.

A pair of constricted portions 62 which gradually narrow the width of the flow path groove 54 are formed on the side parts 60a and 60b so as to inwardly extend at an intermediate position in the extending direction of the flow path groove 54. The pair of constricted portions 62 can temporarily guide the infusion fluid T flowing in the flow path groove 54 to the inner side to thereby increase the amount of the infusion fluid T guided by the rib 56.

The connector 10 is basically configured as described above. Next, an operation and an effect when using the connector 10 will be described. As described above, the connector 10 can connect the first to third tubes 20a to 20c to perform fluid infusion. However, since the connector 10 according to the first embodiment can obtain a larger effect when the third tube 20c is not connected thereto, a case where only the first tube 20a and the second tube 20b are connected to the connector 10 will be described in detail in the following description.

FIG. 7A is a side cross-sectional view schematically illustrating the flow of the infusion fluid T in the connector 10 according to the first embodiment; and FIG. 7B is a main part enlarged plan view schematically illustrating the flow of the infusion fluid T in the connector 10 according to the first embodiment.

In the connector 10, the first tube 20a (refer to FIG. 1) is connected to the first port 28 located on the upstream side, and the second tube 20b (refer to FIG. 1) is connected to the second port 30 located on the downstream side. In this state, the infusion fluid T flows through the connector 10. On the other hand, the third port 32 into which the plug 46 (refer to FIG. 6) of the third tube 20c is inserted is in a blocked state by the valve 44.

The infusion fluid T supplied from an infusion bag flows into the connector 10 through the first tube 20a. Then, as illustrated in FIG. 7A, the infusion fluid T passes through the main line flow path 38 inside the connector 10, and flows out of the connector 10. Then, the infusion fluid T is administered (supplied) to a living body through an indwelling needle which is connected to the downstream side of the connector 10.

In this case, inside the connector 10, the infusion fluid T flows from the inside of the first tube 20a into the first port flow path 34, and advances straight (linearly moves) toward the downstream side (the connector base 24) along the first port flow path 34.

The infusion fluid T that has moved to the connector base 24 linearly flows into the flow path groove 54. Then, the movement of the infusion fluid T is guided in a predetermined direction by the rib 56 which is provided in a standing manner at the intermediated position in the extending direction of the flow path groove 54.

Specifically, as illustrated in FIG. 7B, the infusion fluid T that has moved from the upstream side (the left side in FIG. 7B) moves in an oblique direction by one of the wall surfaces 56a which obliquely extends in plan view. That is, the infusion fluid T is guided so as to flow toward the side part 60b having depth from the side part 60a located on the front side along the wall surface 56a of the rib 56 which is opposed to a travelling direction of the infusion fluid T. Therefore, the travelling direction of the infusion fluid T is inclined toward the side part 60b with respect to the axial direction of the main line flow path 38.

As illustrated in FIG. 7A, since the rib 56 (wall surface 56a) is provided in a standing manner so as to extend upward from the bottom part 58, the travelling direction of the infusion fluid T that has advanced straight from the first port flow path 34 is inclined upward. In this case, since the wall surface 56a of the rib 56 has the curved portion 56b at the coupled part with the bottom part 58, it is possible to smoothly guide the infusion fluid T upward from the bottom part 58.

In this manner, the infusion fluid T is guided by the wall surface 56a in the lateral direction (a direction to flow toward the side part 60b) and in the upper direction. As a result, the infusion fluid T flows obliquely upward, and therefore easily flows into the connection side space 52. Further, the infusion fluid T is concentrated on a part of the connection side space 52 (near above the side part 60b in FIG. 7B) by the obliquely upward flow. Inside the connection side space 52, the infusion fluid T that has been guided so as to be concentrated on a part of the connection side space 52 flows around in the circumferential direction by the inner wall 53 opposed thereto. As a result, a large flow (turbulence of fluid) is generated inside the connection side space 52.

As described above, in a connection side space of a connector, since the flow of fluid (infusion fluid or air bubbles) is not generated, a phenomenon such that fluid stagnates inside the connection side space (stagnating fluid) occurs. A conventional connector (refer to Japanese Unexamined Patent Application Publication (Translation of PCT Application) No. 2010-505551, for example) simply guides an infusion fluid upward. Therefore, since the guided infusion fluid relatively calmly flows inside the connection side space, the infusion fluid hardly affects the stagnating fluid and flows out to the downstream side. Therefore, it has been difficult to discharge the stagnating fluid from the connection side space.

On the other hand, the rib 56 according to the present invention guides the infusion fluid T obliquely upward with respect to the axial direction of the main line flow path 38. That is, by directing the infusion fluid T not only to the upper direction, but also to the lateral direction by the rib 56, a flow in the circumferential direction (lateral direction) is generated inside the connection side space 52. Accordingly, it is possible to make turbulence of the entire fluid inside the connection side space 52 large to accelerate the flow, thereby agitating stagnating fluid. In other words, fluid (infusion fluid or air bubbles) that stagnates inside the connection side space 52 is easily mixed into the infusion fluid T.

In particular, a relatively large amount of stagnating fluid exists near the inner wall 53 of the connection side space 52. However, as described above, since the infusion fluid T flows along the circumferential direction of the inner wall 53, it is possible to efficiently allow stagnating fluid to flow. Further, the infusion fluid T containing stagnating fluid moves from the connection side space 52 to the opposite side (downstream side) in the flow path groove 54 beyond the rib 56. As a result, the stagnating fluid can be discharged from the connection side space 52.

The infusion fluid T containing the stagnating fluid flows from the flow path groove 54 into the second port flow path 36, linearly moves along the second port flow path 36, and flows out into the second tube 20b located on the downstream side.

A necessary process can be performed on the infusion fluid T containing the stagnating fluid that has flown out of the connector 10 according to the kind of the stagnating fluid and the condition of the fluid infusion. For example, when performing priming of the infusion line, air bubbles (air) are assumed as stagnating fluid inside the connection side space 52. Therefore, it is possible to perform a process of discharging air bubbles in the air vent filter 18. When it is assumed that an infusion fluid that is different from the infusion fluid T to be supplied remains as stagnating fluid inside the connection side space 52, it is possible to perform a process of discharging the infusion fluid T for a predetermined period of time on the downstream side of the connector 10.

As described above, in the connector 10 according to the first embodiment, the wall surface 56a is inclined so as to direct the infusion fluid T to the side part 60b. Accordingly, the infusion fluid T can be guided so that the turbulence of stagnating fluid existing inside the connection side space 52 is made large to accelerate the flow. Therefore, fluid stagnating inside the connection side space 52 can be easily discharged from the connection side space 52 by the infusion fluid T guided by the wall surface 56a. As a result, in the infusion line to which the connector 10 is applied, the safety of fluid infusion can be significantly enhanced, and a desired infusion fluid can be excellently supplied to a patient.

In particular, in the first embodiment, the wall surface 56a is provided in a standing manner from the bottom part 58 so as to obliquely extend on the bottom part 58, and the opposite ends thereof are coupled to the pair of side parts 60a and 60b. Accordingly, the entire infusion fluid T flowing in the axial direction of the main line flow path 38 can be directed to one direction. Then, the infusion fluid T directed to one direction is guided to the connection side space 52, thereby making it possible to make the flow (turbulence) of stagnating fluid inside the connection side space 52 larger to accelerate the flow. As a result, it is possible to more efficiently discharge the stagnating fluid inside the connection side space 52.

Further, since the coupled part of the wall surface 56a is formed as the curved portion 56b, even the infusion fluid T flowing on the side of the bottom part 58 of the main line flow path 38 can be easily guided to the connection side space 52. Therefore, the amount of infusion fluid T guided to the connection side space 52 increases, thereby making it possible to make the flow of stagnating fluid inside the connection side space 52 further larger.

Further, the wall surfaces 56a are formed on both sides of the rib 56, the both sides facing the first port flow path 34 and the second port flow path 36 divided by the rib 56. Accordingly, in either case where each of the first port 28 and the second port 30 formed in the housing 22 is attached to the first tube 20a or the second tube 20b, either one of the wall surfaces 56a can be made to face the travelling direction of the infusion fluid T. As a result, connection of the connector 10 can be simplified.

Further, since the constricted portion 62 is formed on the side part 60b of the flow path groove 54, the infusion fluid T can be temporarily gathered to the inner side. Accordingly, it is possible to increase the flow velocity of the infusion fluid T as well as direct the travelling direction of the infusion fluid T obliquely upward. As a result, the infusion fluid T can be easily guided to the connection side space 52.

Second Embodiment

Figure 8:
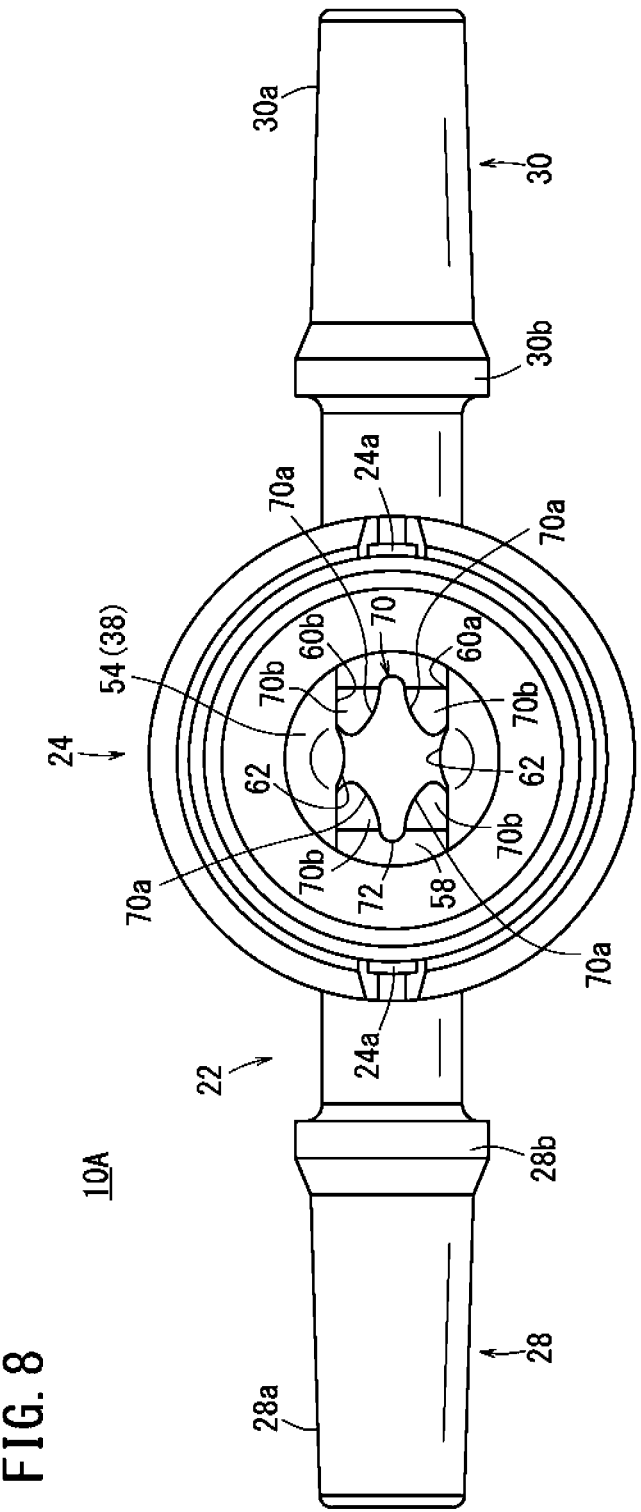
FIG. 8 is a plan view illustrating the entire configuration of a connector according to a second embodiment.

FIG. 8 is a plan view illustrating the entire configuration of the connector 10A according to the second embodiment. In the connector 10A according to the second embodiment described below, the same configurations or configurations achieving the same functions as those of the connector 10 according to the first embodiment will be denoted by the same reference numerals, and description of these configurations will be omitted.

The connector 10A according to the second embodiment is different from the connector 10 according to the first embodiment in that the shape of a rib 70 is formed into a generally cross shape which is different from the shape of the rib 56. More specifically, the rib 70 of the connector 10A is provided in a standing manner on a bottom part 58 of a main line flow path 38, and has a top part 72 located on the central axis of the main line flow path 38 in plan view. A wall surface 70a of the rib 70 is formed so as to obliquely extend from the top part 72 toward a pair of side parts 60a and 60b, and coupled to the pair of side parts 60a and 60b. In this manner, even when the rib 70 is formed into a generally cross shape, it is possible to guide the infusion fluid T so as to generate a large flow inside a connection side space 52 to accelerate agitation of stagnating fluid.

Hereinbelow, an operation of an infusion fluid T flowing through the connector 10A will be specifically described. The infusion fluid T flowing from a first port 28 is divided into two directions from the top part 72 of the rib 70 as a base point, the top part 72 being located on the axis of the main line flow path 38 (flow path groove 54), toward one direction from the top part 72, the side part 60a and toward another direction from the top part 72, the side part 60b. Even when being divided into two directions by the wall surface 70a, the infusion fluid T is guided so as to flow toward the side part 60a and the side part 60b in the respective directions.

Accordingly, the infusion fluid T that has been guided to two oblique directions flows into the connection side space 52, thereby making it possible to make the flow (turbulence) of stagnating fluid large inside the connection side space 52. As a result, also by the wall surface 70a of the second embodiment, stagnating fluid inside the connection side space 52 can be efficiently discharged.

Further, the wall surface 70a has a curved portion 70b at a position coupled to the bottom part 58. Accordingly, in the same manner as in the curved portion 56b of the rib 56 of the first embodiment, the infusion fluid T can be smoothly guided to the connection side space 52 located above.

Also in the connector 10A, wall surfaces 70a can be formed on both sides of the rib 70, the both sides facing a first port flow path 34 and a second port flow path 36 divided by the rib 70. Therefore, in either case where each of the first port 28 and the second port 30 formed in the housing 22 is attached to the first tube 20a or the second tube 20b, either one of the wall surfaces 70a can be made to face the travelling direction of the infusion fluid T. As a result, connection of the connector 10A can be simplified.

Reference Example

Figure 9:
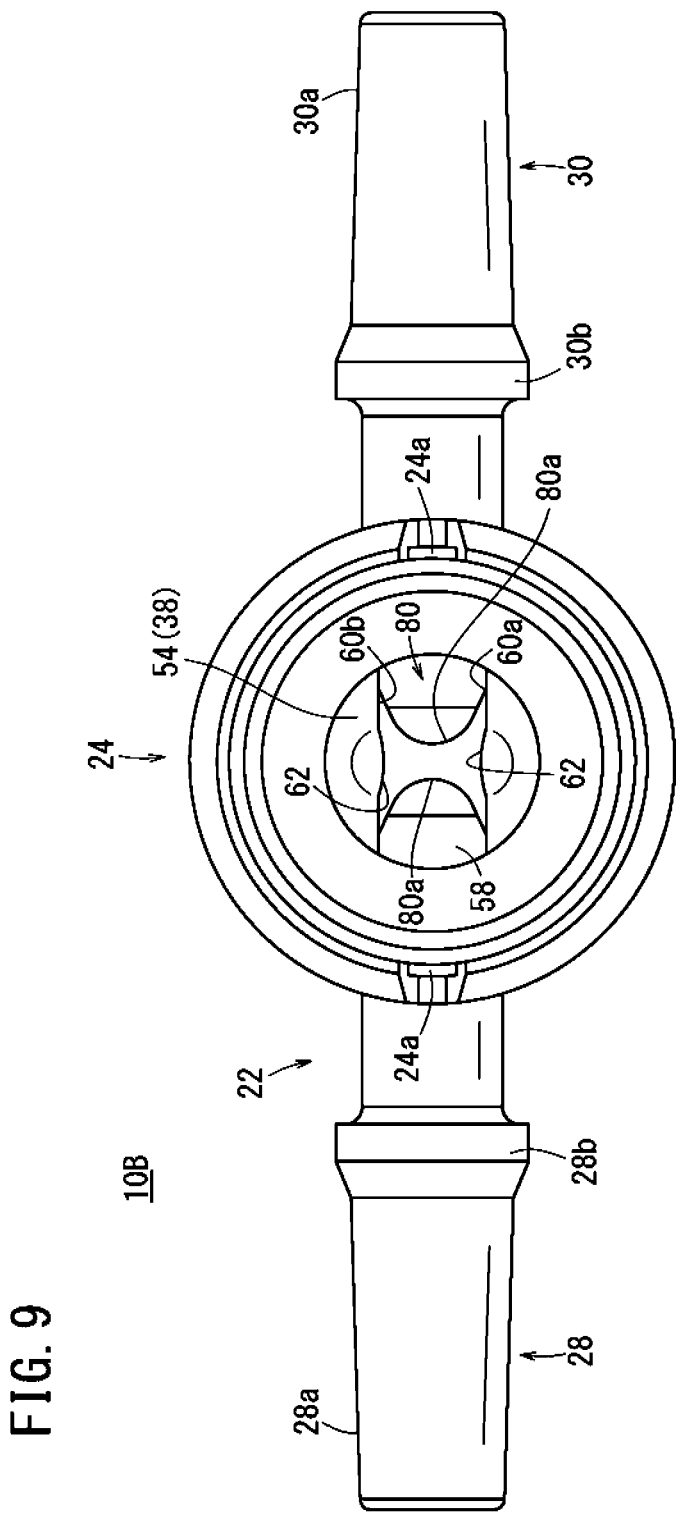
FIG. 9 is a plan view illustrating the entire configuration of a connector as a reference example.

FIG. 9 is a plan view illustrating the entire configuration of a connector 10B as a reference example.

The connector 10B according to the reference example is different from the connector 10 according to the first embodiment and the connector 10A according to the second embodiment in that a central part in the width direction of a rib 80 is formed into a generally recessed shape recessed along the travelling direction. More specifically, a wall surface 80a of the rib 80 is provided in a standing manner on a bottom part 58 of a main line flow path 38, and curved into an arc shape from a pair of side parts 60a and 60b toward the central axis of the main line flow path 38 in plan view. A top part (valley portion 82) of the wall surface 80a on the central axis is the deepest part. It is conceivable that the connector 10B has such a rib 80 (wall surface 80a) formed on the main line flow path 38.

It is needless to say that the connectors 10 and 10A according to the present invention are not limited to the above embodiments, and can have various configurations without departing from the scope of the invention.

What is claimed is:
1. A connector comprising:
a housing;
a main flow path provided inside the housing, the main flow path being configured such that fluid is flowable from a first tube through the main flow path into a second tube; and
a connection terminal including a connection side space that is continuous with the main flow path, the connection terminal being configured such that a third tube is connectable to the connection terminal and an auxiliary flow path of the third tube communicates with the main flow path via the connection side space,
wherein the main flow path includes a main flow path side space that is continuous with at least the connection side space and is defined by:
a bottom part facing the connection side space and a pair of side parts extending from opposite sides of the bottom part toward the connection side space, and
at least one wall surface configured to direct the fluid toward the connection side space and toward the side parts,
wherein the at least one wall surface includes a top part that, when viewed from a connection terminal side of the connector, is located between the side parts,
wherein opposite ends of the at least one wall surface are coupled to the respective side parts wherein, when viewed from the connection terminal side of the connector, the at least one wall surface extends obliquely from the top part toward the respective side parts with respect to an axial direction of the main flow path.

2. The connector according to claim 1, wherein the at least one wall surface has a curved shape at an area at which the at least one wall surface is coupled with the bottom part.

3. The connector according to claim 1, wherein the at least one wall surface comprises a plurality of wall surfaces that are surfaces of a rib dividing the main flow path in plan view into first and second flow paths, the wall surfaces including a first wall surface facing the first flow path and a second wall surface facing the second flow path.

4. The connector according to claim 1, wherein each of the side parts includes a constricted portion that inwardly extends so as to gradually narrow the width of the main flow path side space.

5. The connector according to claim 1, wherein, when viewed from the connection terminal side of the connector, the top part is located on a central axis of the main flow path.

6. A connector comprising:
a housing;
a main flow path provided inside the housing, the main flow path being configured such that fluid is flowable from a first tube through the main flow path into a second tube; and
a connection terminal including a connection side space that is continuous with the main flow path, the connection terminal being configured such that a third tube is connectable to the connection terminal and an auxiliary flow path of the third tube communicates with the main flow path via the connection side space,
wherein the main flow path includes a main flow path side space that is continuous with at least the connection side space and is defined by:
a bottom part facing the connection side space and a pair of side parts extending from opposite sides of the bottom part toward the connection side space, and
at least one wall surface configured to direct the fluid toward the connection side space and toward at least one of the side parts,
wherein the at least one wall surface is in a fixed location with respect to the first and second tubes, and, when viewed from the connection terminal side of the connector, extends obliquely with respect to an axial direction of the main flow path.

7. A connector comprising:
a housing;
a main flow path provided inside the housing, the main flow path being configured such that fluid is flowable from a first tube through the main flow path into a second tube; and
a connection terminal including a connection side space that is continuous with the main flow path, the connection terminal being configured such that a third tube is connectable to the connection terminal and an auxiliary flow path of the third tube communicates with the main flow path via the connection side space,
wherein the main flow path includes a main flow path side space that is continuous with at least the connection side space and is defined by:
a bottom part facing the connection side space and a pair of side parts extending from opposite sides of the bottom part toward the connection side space, and
at least one wall surface configured to direct the fluid toward the connection side space and toward at least one of the side parts,
wherein at least a portion of the at least one wall surface extends toward the connection terminal in a direction perpendicular to a surface of the bottom part that faces the connection side space.

\* \* \* \* \*